United States Patent [19]

Leone-Bay

[11] Patent Number: 4,825,012

[45] Date of Patent: Apr. 25, 1989

[54] INVERSION OF ALLYLIC ALCOHOLS

[75] Inventor: Andrea Leone-Bay, Ridgefield, Conn.

[73] Assignee: Akzo America Inc., New York, N.Y.

[21] Appl. No.: 129,494

[22] Filed: Dec. 7, 1987

[51] Int. Cl.$^4$ .................. C07C 29/58; C07C 33/03
[52] U.S. Cl. .................................. 568/902; 568/813; 568/875; 568/909.5
[58] Field of Search ............... 568/813, 902 R, 840 B, 568/909.5, 903, 875

[56] References Cited

U.S. PATENT DOCUMENTS

| | | | |
|---|---|---|---|
| 4,006,193 | 2/1977 | Ninagawa et al. | 568/840 B |
| 4,087,472 | 5/1978 | Hughes | 568/813 |
| 4,219,683 | 8/1980 | Wu | 568/813 |
| 4,254,291 | 3/1981 | Kane | 568/902 R |

FOREIGN PATENT DOCUMENTS

| | | | |
|---|---|---|---|
| 70618 | 1/1983 | European Pat. Off. | 568/813 |
| 128341 | 7/1984 | Japan | 568/902 R |

*Primary Examiner*—J. E. Evans
*Attorney, Agent, or Firm*—Richard P. Fennelly; Louis A. Morris

[57] ABSTRACT

Allylic 1-hydroxy alcohols are inverted to allylic 3-hydroxy alcohols by: (1) epoxidizing the allyl group of the allylic 1-hydroxy alcohol to the corresponding 2,3-epoxy-1-hydroxy alcohol; (2) transforming the 2,3-epoxy-1-hydroxy alcohol compound to a 1,2-dihalo-3-hydroxy alcohol; and (3) dehalogenating the 1,2-dihalo-3-hydroxy alcohol to form the desired allylic 3-hydroxy alcohol.

2 Claims, No Drawings

INVERSION OF ALLYLIC ALCOHOLS

BACKGROUND OF THE PRESENT INVENTION

1. Field of the Present Invention

The present invention relates to the inversion of allylic 1-hydroxy alcohols to allylic 3-hydroxy alcohols.

2. Description of the Prior Art

The present invention relates to the inversion of allylic 1-hydroxy alcohols of the structure $R_2C=CR-CR_2OH$ where R is hydrogen or a suitable organic radical (e.g., substituted or unsubstituted alkyl, aryl, heterocyclic, etc.) capable of bonding to carbon to give the corresponding allylic 3-hydroxy alcohol of the structure $R_2C(OH)CR=CR_2$. This inversion reaction will find utility in organic syntheses reactions in the agricultural chemical, pharmaceutical, and specialty chemical areas where such an inversion reaction (or transposition reaction) is needed.

In Tetrahedron Letters, No. 30, pp. 2621-2622 (1976) A. Yasuda et al. discuss a stereoselective 1,3-transposition reaction of allylic alcohols where an allylic 1-hydroxy alcohol, of the above-described general structure, is converted to the above-described allylic 3-hydroxy alcohol. The Yasuda et al. process involves the initial epoxidation of the allylic group of the allylic 1-hydroxy alcohol to form the corresponding epoxy compound, the subsequent formation of the epoxy mesylate therefrom, and the subsequent elimination of the epoxy mesylate (e.g., by reaction with sodium and liquid ammonia) to form the desired allylic 3-hydroxy alcohol. As used herein, the nomenclature "1", "2" and "3" in identifying the three carbon allylic configuration (C=C—C) is fixed in regard to allylic alcohols by having the alcoholic hydroxy group (—OH) on the "1" carbon atom. In such cases, the unsaturated carbon-to-carbon bond stretches from the "2" carbon atom to the "3" carbon atom.

SUMMARY OF THE PRESENT INVENTION

The present inversion reaction affects the same type of transposition described in the Yasuda et al. publication by treating the type of epoxy 1-hydroxy alcohol formed in the initial reaction step described therein to form a transposed 1,2-dihalo 3-hydroxy alcohol reaction product therefrom followed by dehalogenating such a product to form the desired allylic 3-hydroxy alcohol. As used herein, the term "allyl" or "allylic" is intended to refer to the general grouping

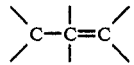

as represented in the structural formula indicated above.

The first step in the present process, like that described by Yasuda et al., involves the epoxidation of the allyl group in the allylic 1-hydroxy alcohol so that the corresponding 2,3-epoxy-1-hydroxy alcohol results. This epoxidation reaction can be carried out using conventional epoxidation techniques (e.g., as described in J. Amer. Chem. Soc. 95, 6136 (1973), and J. Amer. Chem. Soc. 96, 5254 (1974)).

The next step in the instant process involves formation of the inverted or transposed 1,2-dihalo-3 hydroxy alcohol from the 2,3-epoxy-1-hydroxy alcohol. This can be accomplished by use of halogen (e.g., bromine) and triphenyl phosphine in benzene at reaction temperatures conducive to the reaction (e.g., 0°-25° C.). The resulting product has the formula $R_2C(OH)CRXCR_2X$, with X being halogen and R being as defined above.

The product from the preceding step is then subjected to a conventional dehalogenation step using such reagents as zinc and acetic acid (e.g., as described in Org. Synth. (1963) Coll. Vol. 4, 195 and J. Org. Chem. (1970) 35, 1733). This places an allylic bond between the two most terminal carbon atoms which previously held the halogen atoms.

The present invention is further illustrated by the Example which follows.

EXAMPLE

This Example illustrates the conversion of a 1-hydroxy-2,3-epoxide into a 1,2-dibromo-3-hydroxide using triphenylphosphine-bromine.

Bromine (1.06 grams, 6.7 millimoles) was added to a solution of triphenylphosphine (1.75 grams, 6.7 millimoles) in benzene (10 milliliters) at 0° C. After stirring 30 minutes, glycidol (1 gram, 6.7 millimoles) was then added. The reaction mixture was allowed to come to room temperature, was stirred for 12 hours, and was then concentrated in vacuo. The resulting yellow oil was subjected to medium pressure liquid chromatography on silica gel using ethyl acetate-hexane (3:7) as the eluting solvent. The desired 1,2-dibromo-3-hydroxy-3-phenylpropane (1.3 grams, 67% yield) was isolated as a yellow oil which darkened on standing.

Allylic alcohols can be converted to 1-hydroxy-2,3-epoxides by conventional means and the 3-hydroxy-1,2-dibromides formed, as illustrated in this Example, can also be reduced to allylic alcohols by conventional methods.

I claim:

1. A process for the inversion of an allylic 1-hydroxy alcohol to an allylic 3-hydroxy alcohol which comprises:
   (a) epoxidizing the allyl group of the allylic 1-hydroxy alcohol of the formula $R_2C=CR-CR_2-OH$, where R is hydrogen, to form a 2,3-epoxy-1-hydroxy alcohol species;
   (b) halogenating the product from step (a) to form a 1,2-dihalo-3-hydroxy alcohol; and
   (c) dehalogenating the product from step (b) to form the desired allylic 3-hydroxy alcohol of the formula $R_2C(OH)CR=CR_2$.

2. A process as claimed in claim 1 wherein the 1,2-dibromo-3-hydroxy alcohol is formed in step (b).

* * * * *